(12) United States Patent
Behrmann et al.

(10) Patent No.: US 6,319,960 B1
(45) Date of Patent: *Nov. 20, 2001

(54) METHOD FOR HYDROCARBON SYNTHESIS REACTIONS

(75) Inventors: William C. Behrmann, Baton Rouge, LA (US); Kym B. Arcuri, Baton Rouge, LA (US); Charles H. Mauldin, Baton Rouge, LA (US); Mordechay Herskowitz, Beer-Sheva (IL)

(73) Assignee: Exxon Research & Engineering Company, Florham Park, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 07/118,619

(22) Filed: Nov. 6, 1987

Related U.S. Application Data

(62) Division of application No. 06/914,781, filed on Oct. 3, 1986, now abandoned.

(51) Int. Cl.⁷ .................................................. C07C 27/06
(52) U.S. Cl. ........................................................ 518/715
(58) Field of Search ............................................. 585/700

(56) References Cited

U.S. PATENT DOCUMENTS 4,413,064 * 11/1983 Beuther et al. ........................ 518/715
4,599,481 * 7/1986 Post ....................................... 585/700

FOREIGN PATENT DOCUMENTS 855317   8/1985   (ZA) .

* cited by examiner

*Primary Examiner*—Peter D. Mulcahy
(74) *Attorney, Agent, or Firm*—Lerner, David, Littenberg, Krumholz & Mentlik, LLP

(57) ABSTRACT

A method for hydrocarbon synthesis reactions from carbon monoxide and hydrogen using a catalyst pellet which includes a solid core and a coated layer of porous support impregnated with a catalyst which optimizes the CO conversion.

28 Claims, 3 Drawing Sheets

METHOD FOR HYDROCARBON SYNTHESIS REACTIONS

This is a division, of application Ser. No. 06/914,781, filed Oct. 3, 1986, now abandoned.

BACKGROUND OF THE PRESENT INVENTION

This invention relates to a method for converting hydrogen and carbon monoixde to heavy hydrocarbons in a fixed bed reactor by a catalytic reaction where the catalyst pellet is designed so as to optimize the CO conversion and methane selectivity. Selectivity to methane is the percentage of the total CO moles converted.

A metal catalyst (e.g. cobalt or ruthenium) on a support (e.g., titania or silica) which may be promoted by different metals (e.g., rhenium, hafnium and others) are used for synthesis of heavy hydrocarbons from a mixture of carbon monoxide and hydrogen. The principal reaction may be expressed as:

where the distribution of the hydrocarbon products can be approximated by the Flory-Schultz expression. The fraction of oxygenates and olefins in the product is small.

An important consideration in the development of the hydrocarbon synthesis process is to minimize the production of light hydrocarbons ($C_1$–$C_4$), especially of methane. The fraction of methane in the product exceeds that predicted by the Flory-Schultz distribution.

Another important consideration is to maximize the productivity, defined as the number of CO moles converted per unit time and reactor volume, so as to minimize the volume of the reactor in which the reaction is carried out.

Both considerations have been met with available catalyst powder of the size 80–140 mesh (approximately 0.15 mm in diameter). However, additional factors should be considered in the design of a fixed bed reactor; namely, the pressure drop in the reactor, and the removal of the heat generated by the reaction.

These require the design of catalyst pellets which retain the properties of the powder catalyst (80–140 mesh) but are larger in size (>1.0 mm). However, since the reactants have to diffuse through liquid-filled pores, the longer diffusion path may create concentration gradients within the pellet. Such gradients alter the hydrogen to carbon monoxide ratio in the pellet due to the lower diffusivity of the latter. As a result the selectivity to methane, which depends on this ratio, increases considerably. Furthermore, since the rate of reaction depends on the concentration of the two reactants, the productivity is smaller in a pellet than in powder.

Because the pellets have to be used in a fixed bed reactor, the design of the catalyst pellet has to be directed toward minimizing the methane selectivity and maximizing the productivity. The catalyst of the present invention is designed to achieve this purpose.

SUMMARY OF THE PRESENT INVENTION

The present invention is a method for converting hyudrogen and carbon monoxide to heavy hydrocarbons in a fixed bed reactor by a catalytic reaction. The method includes contacting the hydrogen and carbon monoxide in the reactor at reaction conditions with a supported catalyst pellet. The support includes an inert or hollow core and an outer layer of porous inorganic refractory oxide. The outer layer has a thickness determined so as to optimize CO conversion to heavy hydrocarbons so that conversion to methane is maintained at a predetermined level. The thickness is determined by relating the rate of diffusion of the CO and the hydrogen to a rate of reaction in the porous inorganic oxide for a predetermined support geometry, partial pressures, and temperatures. The support may take on many shapes e.g., sphere, ring or semi-circle.

A metal catalyst (e.g. cobalt or ruthenium) on a support (e.g., titania or silica) promoted by different metals (e.g., rhenium, hafnium and others) are used for synthesis of heavy hydrocarbons from a mixture of carbon monoxide and hydrogen.

The concentrations of both hydrogen and carbon monoxide decrease as they diffuse into the pellet due to significant mass transfer resistance inside the pores. The global rate of CO conversion in the pellet decreases. Furthermore, the methane production rate increases which is a result of its dependency on the ratio between the hydrogen to CO concentration which increases in the pellet. This ration increases if the parameter γ (see equation 11 below) is less than unit. This behaviour was observed in Co or Ru catalysts supported on titania, silica or alumina.

At a certain depth in the pellet, the hydrogen to CO ratio reaches values which cause most of the CO to be converted to methane which is detrimental to the process. This depth which is called the optimum rim thickness can be determined from the pellet model. Increasing the rim thickness diverts most of the marginal CO conversion to methane while decreasing the rim thickness decreases the CO conversion significantly. Therefore, for an optimal operation, the optimal rim thickness should be determined.

As will be discussed below with respect to FIGS. 2 and 3, it is not possible to simultaneously maximize CO conversion and minimize methane conversion. However, it is possible to choose a rim thickness so as to optimize CO conversion to heavy hydrocarbons.

The process of the present invention is carried out at a rate of CO conversion to hydrocarbons such that the percentage of methane production is maintained at a predetermined low level so as to make the entire process useful and practical.

As the rim thickness increases above the optimal rim thickness, the marginal increase in CO conversion is accompanied by an increase in the percentage of methane production in the converted carbon monoxide. This is observed in FIGS. 2 and 3 discussed below. At the optimal rim thickness, most of the increase in CO conversion goes into methane production. Since an object of the present invention is to limit methane production in the converted CO, a rim thickness must be chosen at about this value.

The supported catalyst may be fabricated by a number of different methods known in the art, see e.g., Scientific Basis For the Preparation of Heterogenous Catalyst, Preprints of the Fourth International Symposium, Sep. 1–4, 1986, Louvain-La-Nueve, Belgium.

DESCRIPTION OF THE PREFERRED EMBODIMENT

Figure 1:
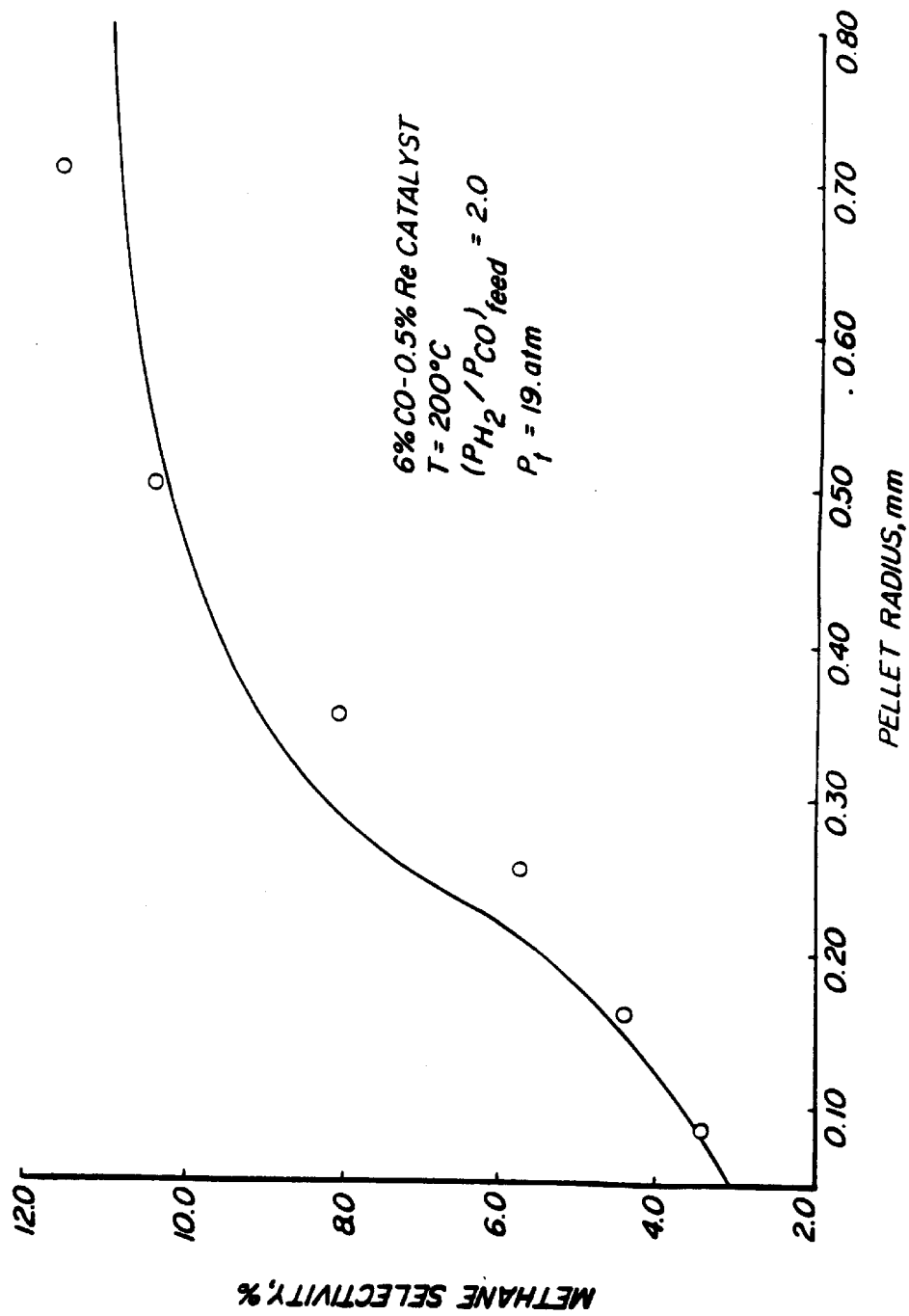
FIG. 1 shows the model predictions for methane selectivity as a function of pellet radius compared with experimental data.

The two reactants, hydrogen and carbon monoxide, diffuse in the liquid filled pores to reach the active metal sites on the support. The function of the support is to increase the surface area which is equal to about 20 m²/g in this case. At steady-state, the fluxes of the two reactants in the pores are equal (since there is no accumulation):

$$\beta D_{e,co}\frac{dC_{co}}{d\chi} = D_{e,H}\frac{dC_H}{d\chi} \quad (1)$$

where the flux is expressed as a product of the effective diffusivity $D_e$ and the concentration gradient. $\beta$ is the stoichiometric coefficient which is equal to 2.07 for the hydrocarbon synthesis reaction. The ratio of the gradients depends on the ratio of the two diffusivities. Since the diffusivity of hydrogen is greater than that of carbon monoxide, the hydrogen to carbon monoxide ratio is expected to increase, moving from the pellet surface towards its center.

A differential mass balance inside the pellet pores for the carbon monoxide (which is the limiting reactant, namely it is depleted before the other reactant) yields:

$$D_{e,co}\frac{1}{\chi^s}\frac{d}{d\chi}\left(\chi^s\frac{dC_{co}}{d\chi}\right) = \rho_p r_{co} \quad (2)$$

where X is the radial position measured from the external surface toward the center, $P_p$ is the pellet density $C_{co}$ is the CO concentration in the liquid-filled pores and $r_{co}$ is the intrinsic rate of reaction on the active sites. s is equal to two for a sphere and to unity for a cylinder. This analysis has been carried out for a sphere or a cylinder. However, the analysis can be early extended to three shapes. For example, rims having a ring shape or a semi-circular shape may be used.

The boundary condition on the external surface is:

$$C_{co}=P_{co,b}/H_{co} \quad X=X_s \quad (3)$$

where $P_{co,b}$ is the CO partial pressure in the bulk gas phase and $H_{co}$ is the Henry's law constant. The other boundary condition is set in two cases:

1. inert core $$\frac{dC_{co}}{d\chi} = o \quad \chi = \chi_i \quad (4)$$

2. hollow core $$C_{co}=P_{co,b}/H_{co} \quad X=X_i; \quad (5)$$

In the deviation of the boundary conditions it is assumed that the external mass transfer resistance is negligible. This assumption was tested both experimentally and theoretically. Furthermore, the pellet is assumed to be isothermal, based on calculations which indicated temperature gradients less than 0.1° C., as expected for liquid-filled porous catalysts.

Equation (2) is general for any reaction with diffusion, while the rate of reaction depends on the catalyst system. The intrinsic rate expression (free of internal or external mass transfer resistance) for catalyst systems such as cobalt or ruthenium on titania or silica can be written as:

$$r_{co} = k_1\exp\left(-\frac{E_1}{RT}\right)\frac{P_{co}^a P_H^b}{(1+k_2P_{co}+k_3P_H)^2} \quad (6)$$

The values of $k_1$, $k_2$, $k_3$, $E_1$, a, b and c are calculated from kinetic rate data obtained in laboratory reactors. The kinetic parameter $k_1$ usually depends only on the metal concentration on the support. However, in certain cases such as cobalt on titania, it is also a function of the water partial pressure:

$$k_1 = A\frac{1+k_4P_{H_2O}}{1+(k_5P_{H_2O})^2} \quad (7)$$

where A is the activity of the catalyst.

Equation (6) can be expressed in terms of the CO and $H_2$ concentrations using the Henry's law:

$$C_{co}=P_{co}/H_{co}; \quad C_H=P_H/H_H \quad (8)$$

Furthermore, the $H_2$ concentration can be expressed in terms of the CO concentration by integrating equation (1) to give $$C_H = \frac{P_{H,b}}{H_H} - \frac{\beta D_{e,co}}{D_{e,H}}\left(\frac{P_{co,b}}{H_{co}} - C_{co}\right) \quad (9)$$

or $$\frac{H_H C_H}{P_{H,b}} = 1 - \alpha\left(1 - \frac{H_{co}C_{co}}{P_{co,b}}\right) \quad (10)$$

where $$\alpha = \frac{\beta D_{e,co}}{D_{e,H}}\frac{H_H}{H_{co}}\frac{P_{co,b}}{P_{H,b}} \quad (11)$$

Substituting equations (6) and (10) into equation (2) and expressing the equation in dimension-less form yields the dimensionless number $$\phi = (\chi_s - \chi_c)\left[\frac{\rho_p k_1\exp\left(-\frac{E_1}{RT}\right)H_{co}P_{H,b}}{D_{e,co}(k_2P_{co,b})^c}\right]^{\frac{1}{2}} \quad (12)$$

$\phi$, called the Thiele modulus, is the ratio between the maximum rate of reaction and the maximum rate of diffusion. If $\phi \gg 1$ the process is diffusion limited while for $\phi \ll 1$ the process is kinetic limited. Since $\phi$ is directly proportional to the thickness of the active layer or rim, diffusion is important in pellets and negligible in powder. The other factors affecting $\phi$ are the partial pressures, temperature and the catalyst activity (metal loading).

$\gamma$ expresses the ratio between the maximum rate of diffusion of the two reactants. If $\gamma=1$, the ratio of carbon monoxide to hydrogen remains unchanged in the pores while for $\gamma<1$ this ratio decreases.

Equation (2) is solved to yield the concentration profiles in the pores of the pellet. Then the concentration profiles are integrated over the volume of the pellet to calculate the effectiveness factor which is the ratio of the actual rate of reaction (called the global rate of reaction) and the maximum rate reaction calculated at the surface conditions:

$$\eta_{co} = \frac{\frac{1}{v}\int_{V_p} r_{co} dV}{r_{co}(P_H, P_{co}, P_{H_2O})} \quad (13)$$

The same concentration profiles are integrated using the rate of methane production rate $r_{CH_4}$ to yield the effectiveness factor for methane $$\eta_{CH_4} = \frac{\frac{1}{V_p}\int_{V_p} r_{CH_4} dV}{r_{CH_4}(P_H, P_{Co}, P_{H_2O})} \quad (14)$$

$r_{CH_4}$ was also obtained from kinetic measurements:

$$r_{CH_4} = k_4 \exp\left(\frac{-(E_2 - E_1)}{RT}\right) \frac{P_H}{1 + k_2 P_{CO} + k_3 P_H} r_{Co} \quad (15)$$

Finally, $\eta_{co}$ and $\eta_{CH_4}$ are employed in the reactor mass balance to calculate the carbon monoxide conversion and the methane selectivity. For simplicity, the reactor is assumed to be isothermal:

$$y_{Co,i} \frac{G_F}{M_i} \frac{dX_{CO}}{dZ} = \eta_{CO} P_8 r_{CO} \quad (16)$$

$$y_{Co,i} \frac{G_F}{M_i} \frac{dX_{CH_4}}{dZ} = \eta_{CH_4} P_8 r_{CH_4} \quad (17)$$

where $y_{ro,i}$ is the carbon monoxide mole fraction in the feed, $G_f$ is the mass velocity, $M_i$ is the molecular weight of the feed, $P_B$ is the bed density and $x_{co}$ and $x_{CH_4}$ are the carbon monoxide and methane conversion, respectively.

Although the fixed bed reactor is noniso-thermal, the results presented here hold also in this case. Since the temperature increase never exceeds 30° F., the optimal rim thickness can be calculated at the average temperature in the bed.

Estimation of Effective Diffusivities

The carbon monoxide conversion and the methane selectivity were measured with a 6% Co-0.5% Re catalyst of different pellet sizes. The hydrogen to Co ratio of the feed was 2.0. Those data were used to estimate the carbon monoxide and hydrogen effective diffusivities following the procedures:

Values of $C_{e,CO}$ and $D_{e,H}$ were assumed;
The effectiveness factors $\eta_{CO}$ and $\eta_{CH_4}$ were calculated from equations (9) and (10) and the solution of equation (2) given the inlet conditions to the reactor;
Then the carbon monoxide conversion and the conversion to methane were calculated by integrating equations (16) and (17). Since the effectiveness factors are a function of the carbon monoxide, hydrogen and water partial pressures, the effectiveness factors were recalculated along the reactor as the partial pressures changed;
The methane selectivity was calculated from the ratio of the conversion to methane $X_{CH_4}$ and the carbon monoxide conversion $X_{CO}$;
The calculated carbon monoxide conversion and the methane selectivity were compared with the experimental values for the various pellet sizes; and
The effective diffusivities are adjusted to give the best fit of the experimental data. A comparison between the predictions and the data are given in FIG. 1 and Table 1.

EXAMPLE 1

Figure 2:
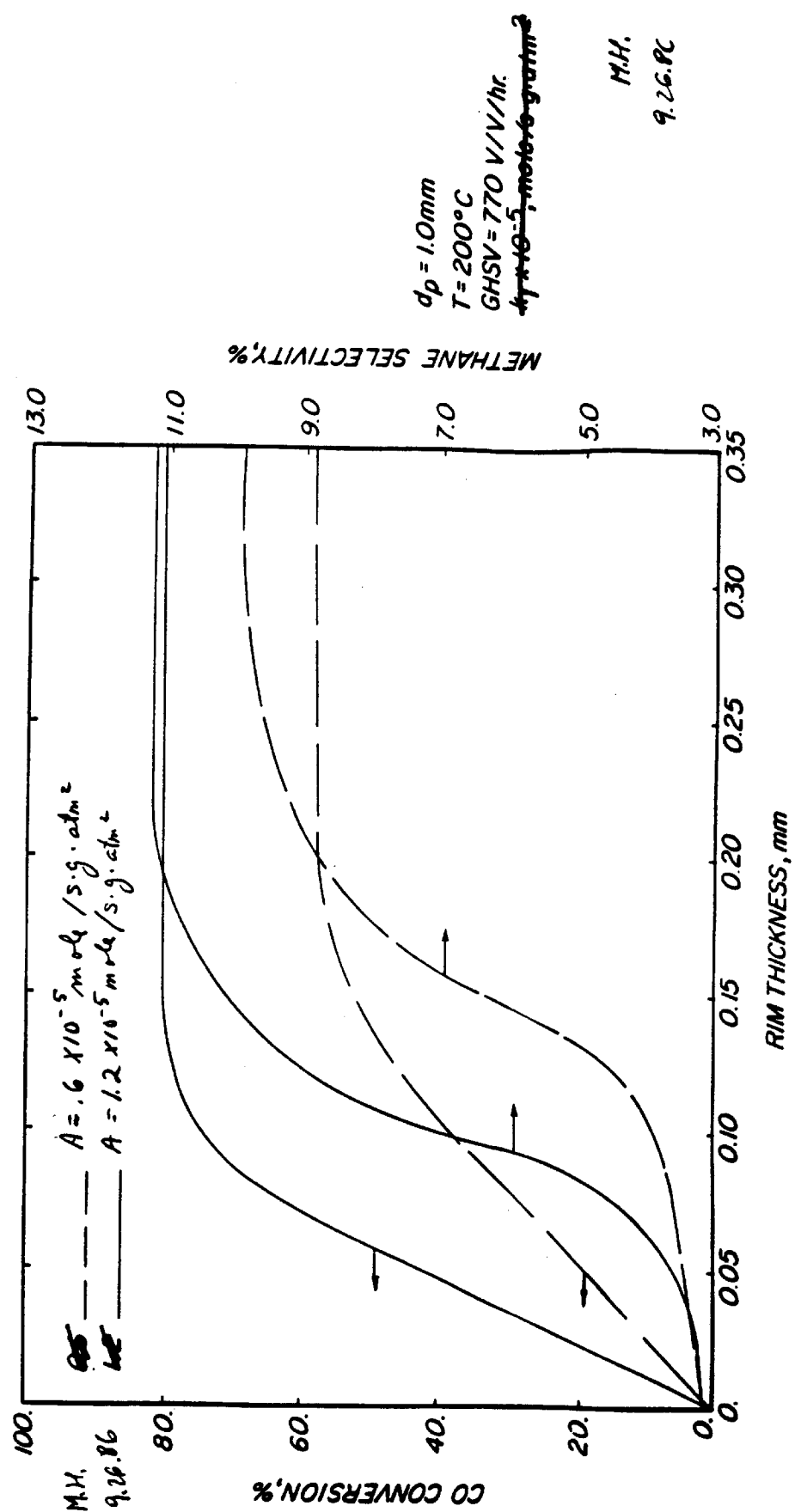
FIG. 2 shows carbon monoxide conversion and methane selectivity as a function of rim thickness for spherical pellets.
Figure 3:
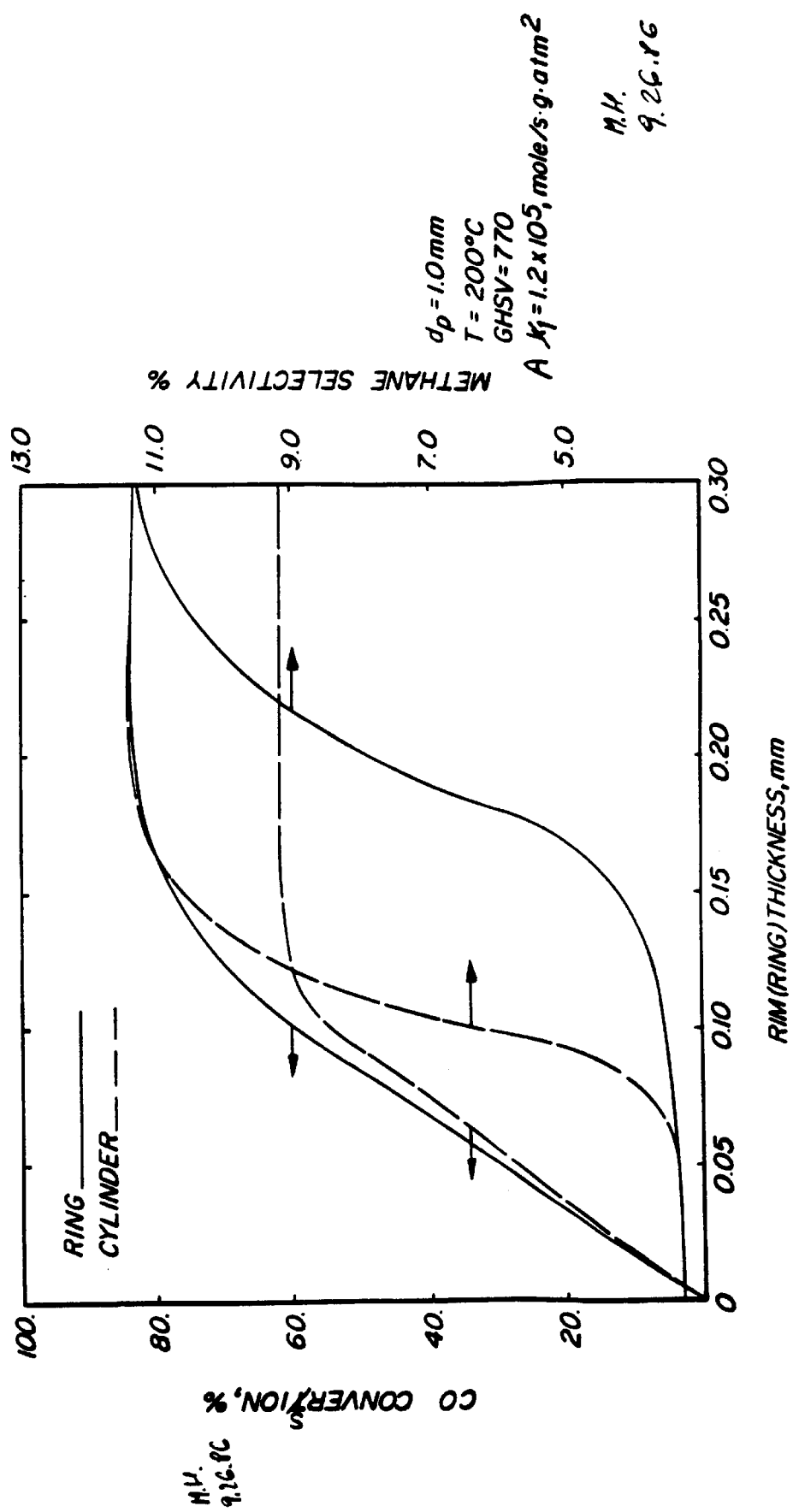
FIG. 3 shows carbon monoxide conversion and methane selectivity as a function of rim thickness for a ring, and cylindrical pellets.

Simulations of the carbon monoxide conversion and methane selectivity as a function of the rim thickness are depicted in FIG. 2 for a spherical pellet loaded with catalysts having two different activities. A hydrogen to Co ratio of 2.0 in the feed was assumed. The carbon monoxide conversion increases with the rim thickness up to its maximum value. The methane selectivity remains almost constant up to certain rim thickness where it increases steeply. Over a range of rim thicknesses the carbon monoxide conversion reaches almost its maximum value while the methane selectivity is still low. Specifically, in FIG. 2 for a spherical pellet with an activity of $6 \times 10^4$ mol/s/g/atm$^2$ the range is 0.13 to 0.15 mm while for an activity of $1.2 \times 10^5$ mol/s/g/atm$^2$ the range is 0.08 to 0.10 mm. This is the essence of the invention. Based on design specification, a rim thickness can be determined to give both a high carbon monoxide conversion and a low methane selectivity. The exact value of the rim thickness depends on the catalyst activity, the partial pressures, the temperature and the pellet shape and configuration. An example of a ring and a cylinder is given in FIG. 3. The behaviour of those pellet is similar in terms of the effect of rim thickness on CO conversion and methane selectivity. The detailed calculations are carried out for each pellet shape using the general reaction and diffusion model.

EXAMPLE 2

Experiments were performed in a reactor 3 ft. long and 0.5 in. in diameter. The reactor was packed with 1 mm dia. spherical catalyst pellets loaded uniformly with 6% Co-0.5% Re. Isothermal conditions were maintained in the reactor.

Data obtained at various temperatures and hydrogen to CO ratios in the feed were compared with the predictions of the model. As explained previously, the carbon monoxide conversion and methane selectivity were obtained by integrating equations (16) and (17) and calculating the effectiveness factors from equations (13) and (14).

In the experiments with a hydrogen to CO ratio in the feed of less than the stoichiometric ratio (2.07), the ratio decreased along the bed. Since the methane selectivity depends on this ratio, it decreased as the hydrogen to CO ratio decreased. Furthermore, since the diffusion in the catalyst pores was one of the limiting steps in this system, a lower hydrogen to CO ratio increases the parameter γ which means a lower methane selectivity. A comparison of experiments 4, 5 and 6 illustrates the improvements in methane selectivity. In experiment 3, the methane selectivity increased as compared with experiment 6 because the temperature was higher. The agreement for both the methane selectivity and the carbon monoxide conversion were good, as shown in Table 2.

EXAMPLE 3

Experiments were performed in a reactor 3 feet long and 0.5 inches in diameter. In this case the reactor was operated under nonisothermal conditions, namely the temperature changed along the reactor. The reactor was packed with a spherical rim pellet with 6% Co-0.5% Re catalylsts (based on the rim mass). The pellet size, rim thickness and catalyst activity are given in Table 3. The pressure was 20 atm.

The prediction of the carbon monoxide conversion and methane selectivity requires the solution of a heat balance for the reactor along with the mass balances in equations (16) and (17). A comparison of the temperature profiles, CO conversion and methane selectivity are given in Table 3.

The data indicate that the CO conversion is close to the maximum conversion attainable for those pellets under the given conditions (73% and 78% for Experiments A and B, respectively). However, the methane selectivity was lower than the 11% expected for those pellets as reported in FIG. 1.

The rim tested in this Example was not of optimal size. A 0.1 mm rim would have lowered the methane selectivity to about 5% while keeping the conversion at about 70%.

Example 4

Simulations were performed for a pellet of ring shape. The operating conditions assumed in the simulations are:
reactor diameter—1.5"
pellet outer diameter—1.5 mm
pellet inner diameter—1.0 mm
gas mass velocity—800 $lb/ft^2/h$
coolant temperature—347° F.
catalyst activity—$1.4\times10^5$ $gmol/s/g/atm^2$
feed composition—64% $H_2$, 32% CO, and 4% $N_2$ The heat balance and the mass balance in equations (16) and (17) were solved to yield the following results:
maximum temperature rise—30° F.
CO conversion—70%
methane selectivity—5.6%

TABLE 1

MODEL PREDICTIONS COMPARED WITH DATA

| Pellet Radius | | Bulk Density | CO Conversion | |
|---|---|---|---|---|
| mm | GHSV* | $g/cm^3$ | exp. | pred. |
| 0.088 | 1500 | 1.47 | 76 | 74 |
| 0.166 | 1320 | 1.47 | 76 | 77 |
| 0.252 | 1000 | 1.53 | 78 | 83 |
| 0.356 | 1140 | 1.59 | 73 | 69 |
| 0.500 | 840 | 1.73 | 75 | 76 |
| 0.705 | 510 | 1.64 | 79 | 81 |

*Gas hourly space velocity.

TABLE 2

PREDICTED AND EXPERIMENTAL SELECTIVITIES AND CONVERSIONS

| Exp. No. | Temp., ° C. | Feed $H_2$/CO | Selectivity, % | | CO Conversion, % | |
|---|---|---|---|---|---|---|
| | | | exp. | pred. | exp. | pred. |
| 1 | 185 | 1.70 | 6.6 | 4.2 | 48 | 52 |
| 4 | 192 | 2.00 | 9.6 | 8.1 | 76 | 76 |
| 2 | 199 | 1.55 | 6.6 | 5.0 | 56 | 57 |
| 3 | 204 | 1.69 | 8.1 | 7.7 | 63 | 65 |
| 4 | 193 | 2.19 | 10.2 | 10.0 | 74 | 74 |
| 5 | 193 | 1.90 | 7.6 | 7.3 | 74 | 76 |
| 6* | 193 | 1.70 | 5.3 | 4.7 | 74 | 76 |

*The activity decreased by about 10%.

TABLE 3

MODEL PREDICTIONS AGREE WITH NON-ISOTHERMAL PELLET DATA $D_p$ = 1.10 mm     Rim Thick. = 0.15 mm
$H_2$/CO in the feed = 2.0
$k_1$ = 12.0 × $10^4$ $gmol/g/s/atm^2$

| | EXPERIMENT A | | EXPERIMENT B | |
|---|---|---|---|---|
| | Exp. | Pred. | Exp. | Pred. |
| Co Conv., mol % | 70.6 | 71.6 | 75.3 | 76.6 |
| $CH_4$ Sel., mol % | 8.5 | 8.4 | 8.5 | 8.9 |

| | TEMPERATURE, ° F. | | | |
|---|---|---|---|---|
| AXIAL POSITION | TH | TH | TH | TH |
| 0.0 | 377 | | 389 | |
| 0.09 | 383 | 385 | 398 | 401 |
| 0.19 | 385 | 387 | 401 | 403 |
| 0.29 | 388 | 388 | 405 | 405 |
| 0.39 | 390 | 390 | 406 | 406 |
| 0.49 | 390 | 390 | 405 | 405 |
| 0.59 | 390 | 390 | 405 | 404 |
| 0.69 | 388 | 389 | 402 | 402 |
| 0.79 | 387 | 388 | 400 | 399 |
| 0.89 | 385 | 387 | 397 | 397 |
| 0.99 | 381 | 385 | 393 | 395 |

What is claimed is:

1. A catalyst for converting CO and $H_2$ to hydrocarbons comprising a particulate metal compound on a support wherein said catalyst support includes an inert or hollow core and an outer layer of porous inorganic refractory oxide, said layer having a thickness determined to maximize CO conversion and minimize methane conversion wherein said thickness is determined by relating the rate of diffusion of said CO and $H_2$ to a rate of reaction at a predetermined temperature, partial pressures, support geometry and catalyst type and preparation.

2. The catalyst of claim 1 wherein said catalyst is ruthenium.

3. The catalyst of claim 1 wherein said catalyst is cobalt.

4. The catalyst of claim 1 wherein said catalyst support has the shape of a sphere.

5. The catalyst of claim 1 wherein said catalyst support has the shape of a ring.

6. The catalyst of claim 1 wherein said catalyst support has the shape of a cylinder.

7. The catalyst of claim 1 wherein said catalyst support has the shape of a semi-circle.

8. A process for the preparation of hydrocarbons by catalytic reaction of carbon monoxide with hydrogen, wherein a mixture of carbon monoxide and hydrogen is contacted at reaction conditions with a catalyst comprising a pellet containing cobalt and a support wherein the cobalt is contained in an outer layer of the catalyst and the thickness of the outer layer is selected to maximize carbon monoxide conversion to heavy hydrocarbons and minimize the conversion of carbon monoxide to methane.

9. The process of claim 8 wherein said support has the shape of a sphere.

10. The process of claim 8 wherein said support has the shape of a ring.

11. The process of claim 8 wherein said support has the shape of a cylinder.

12. The process of claim 8 wherein said support has the shape of a semicircle.

13. A process for the preparation of heavy hydrocarbons by catalytic reaction of carbon monoxide with hydrogen, wherein a mixture of carbon monoxide and hydrogen is contacted at reaction conditions with a catalyst comprising a pellet containing a metal and a support wherein the metal is contained in an outer layer of the catalyst and the thickness of the outer layer is selected to maximize carbon monoxide conversion to heavy hydrocarbons and minimize the conversion of carbon monoxide to methane.

14. The process of claim 13 wherein said metal is selected from the group consisting of cobalt and ruthenium.

15. The process of claim 14 including a metal selected from the group consisting rhenium and hafnium.

16. A catalyst comprising a pellet containing a metal and a support wherein the metal is contained in an outer layer of the catalyst and the distribution of the metal throughout the catalyst is selected to maximize carbon monoxide conversion to heavy hydrocarbons and minimize conversion of carbon monoxide to lower hydrocarbons.

17. The catalyst of claim 16 wherein said metal comprises ruthenium.

18. The catalyst of claim 16 wherein said metal comprises cobalt.

19. The catalyst of claim 17 including an additional metal selected from the group consisting of rhenium and hafnium.

20. The catalyst of claim 18 including an additional metal selected from the group consisting of rhenium and hafnium.

21. A process for the preparation of heavy hydrocarbons by catalytic reaction of carbon monoxide with hydrogen, wherein a mixture of carbon monoxide and hydrogen is contacted at reaction conditions with a catalyst comprising a pellet containing a metal and a support having an outer surface, wherein the diffusion path of the carbon monoxide and the hydrogen from said outer surface to said cobalt within said support is selected to maximize carbon monoxide conversion to heavy hydrocarbons and to minimize the conversion of carbon monoxide to methane.

22. The process of claim 21 wherein said method is selected from the group consisting of cobalt and ruthenium.

23. The process of claim 22 including a metal selected from the group consisting of rhenium and hafnium.

24. A catalyst for converting carbon monoxide and hydrogen to hydrocarbons comprising a pellet containing a metal and a support having an outer surface, said support having a diffusion path from said outer surface to said metal selected to maximize carbon monoxide conversion to heavy hydrocarbons and to minimize the conversion of carbon monoxide to methane.

25. The catalyst of claim 24 wherein said metal comprises ruthenium.

26. The catalyst of claim 24 wherein said metal comprises cobalt.

27. The catalyst of claim 26 including an additional metal selected from the group consisting of rhenium and hafnium.

28. The catalyst of claim 26 including an additional metal selected from the group consisting of rhenium and hafnium.

* * * * *

UNITED STATES PATENT AND TRADEMARK OFFICE
CERTIFICATE OF CORRECTION

PATENT NO. : 6,319,960 B1
DATED : November 20, 2001
INVENTOR(S) : Behrmann et al.

It is certified that error appears in the above-identified patent and that said Letters Patent is hereby corrected as shown below:

Column 2,
Line 12, delete "are" and insert therefor -- is --.
Line 23, delete "unit" and insert therefor -- unity --.

Column 3,
Line 32, after "density" insert -- , --.

Column 5,
Line 30, insert -- $Z=0$, $X_{CH4}=0$, $X_{CO}=0$ --.

Column 6,
Line 24, "pellet" should read -- pellets --.
Line 65, "catalylsts" should read -- catalysts --.

Column 9,
Line 11, after "consisting" insert -- of --.

Column 10,
Line 4, delete "cobalt" and insert therefor -- metal --.
Line 8, delete "method" and insert therefor -- metal --.
Line 23, delete "26" and insert therefor -- 25 --.

Signed and Sealed this

Ninth Day of July, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

| | | |
|---|---|---|
| PATENT NO. | : 6,319,960 B1 | Page 1 of 14 |
| APPLICATION NO. | : 07/118619 | |
| DATED | : November 20, 2001 | |
| INVENTOR(S) | : William C. Behrmann et al. | |

It is certified that error appears in the above-identified patent and that said Letters Patent is hereby corrected as shown below:

Add Figure 4 as shown below:

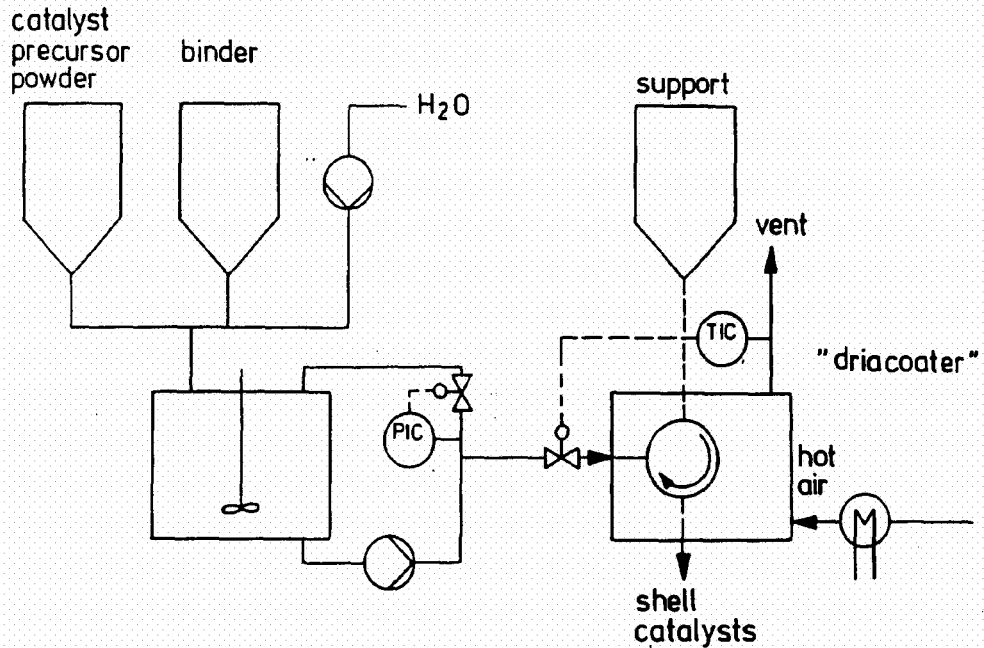

FIGURE 4

UNITED STATES PATENT AND TRADEMARK OFFICE
CERTIFICATE OF CORRECTION

PATENT NO.       : 6,319,960 B1
APPLICATION NO.  : 07/118619
DATED            : November 20, 2001
INVENTOR(S)      : William C. Behrmann et al.

It is certified that error appears in the above-identified patent and that said Letters Patent is hereby corrected as shown below:

Add Figure 5 as shown below:

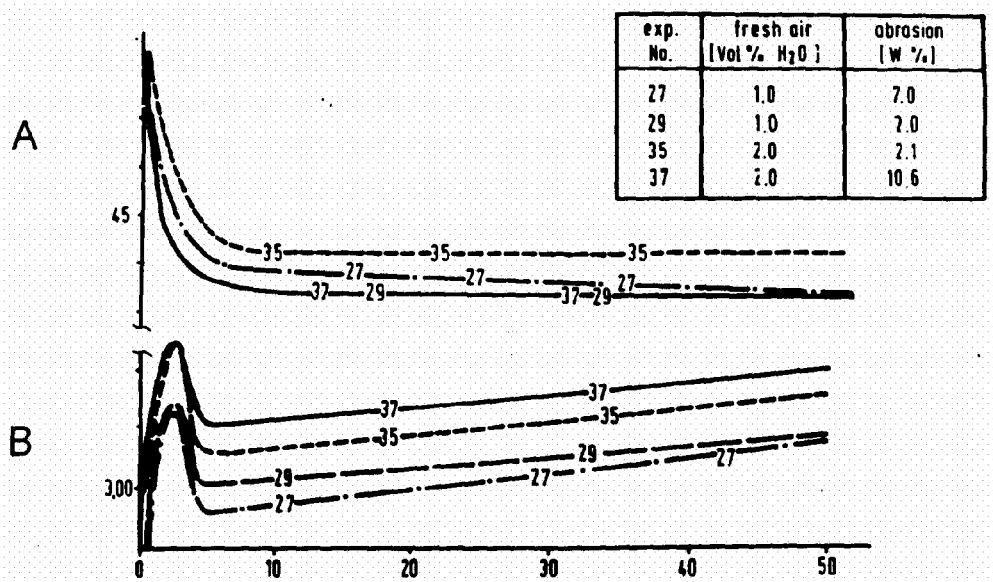

FIGURE 5

UNITED STATES PATENT AND TRADEMARK OFFICE
CERTIFICATE OF CORRECTION

| | |
|---|---|
| PATENT NO. | : 6,319,960 B1 |
| APPLICATION NO. | : 07/118619 |
| DATED | : November 20, 2001 |
| INVENTOR(S) | : William C. Behrmann et al. |

It is certified that error appears in the above-identified patent and that said Letters Patent is hereby corrected as shown below:

Add Figure 6 as shown below:

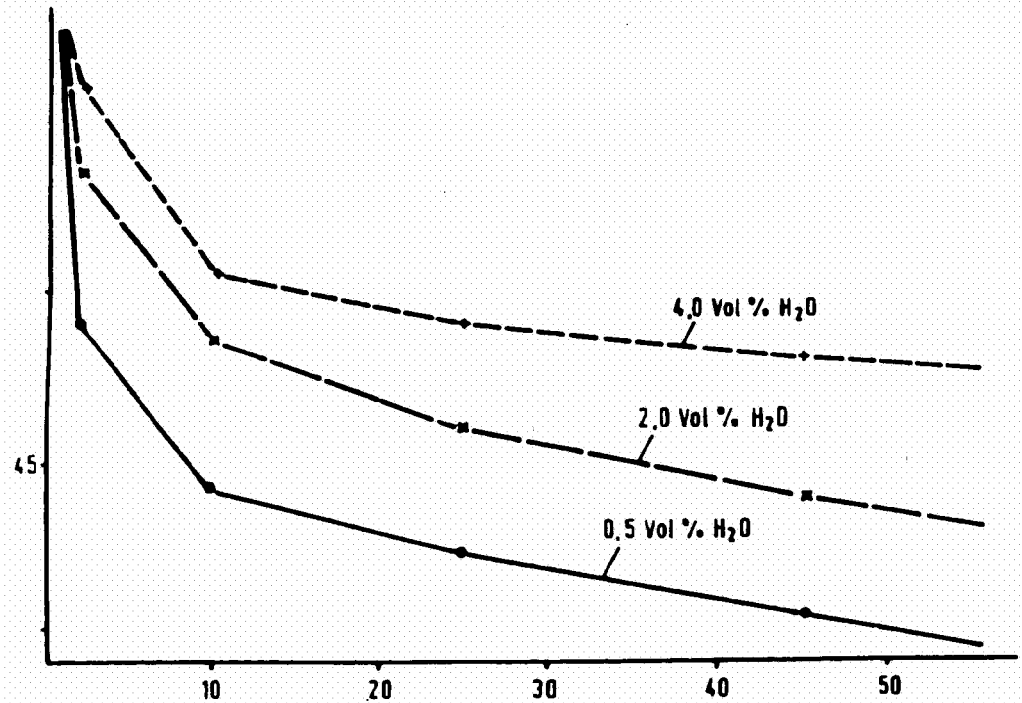

FIGURE 6

UNITED STATES PATENT AND TRADEMARK OFFICE
CERTIFICATE OF CORRECTION

PATENT NO.        : 6,319,960 B1
APPLICATION NO. : 07/118619
DATED             : November 20, 2001
INVENTOR(S)       : William C. Behrmann et al.

It is certified that error appears in the above-identified patent and that said Letters Patent is hereby corrected as shown below:

Add Figure 7 as shown below:

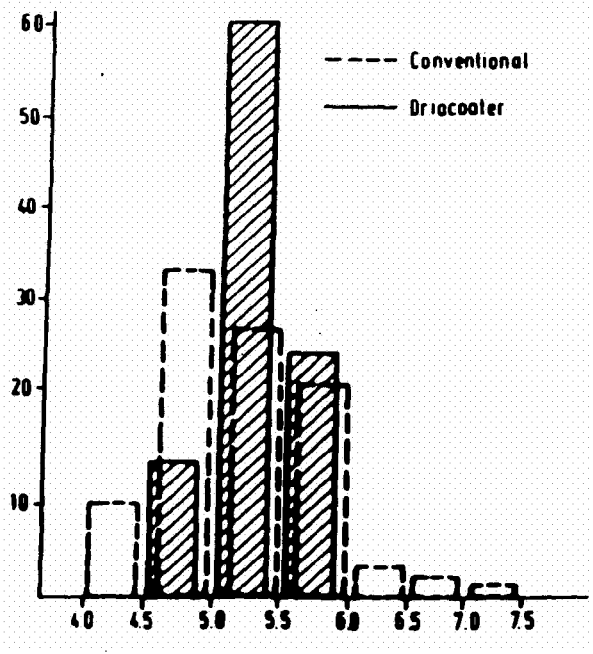

UNITED STATES PATENT AND TRADEMARK OFFICE
CERTIFICATE OF CORRECTION

PATENT NO. : 6,319,960 B1
APPLICATION NO. : 07/118619
DATED : November 20, 2001
INVENTOR(S) : William C. Behrmann et al.

It is certified that error appears in the above-identified patent and that said Letters Patent is hereby corrected as shown below:

Add Figure 8 as shown below:

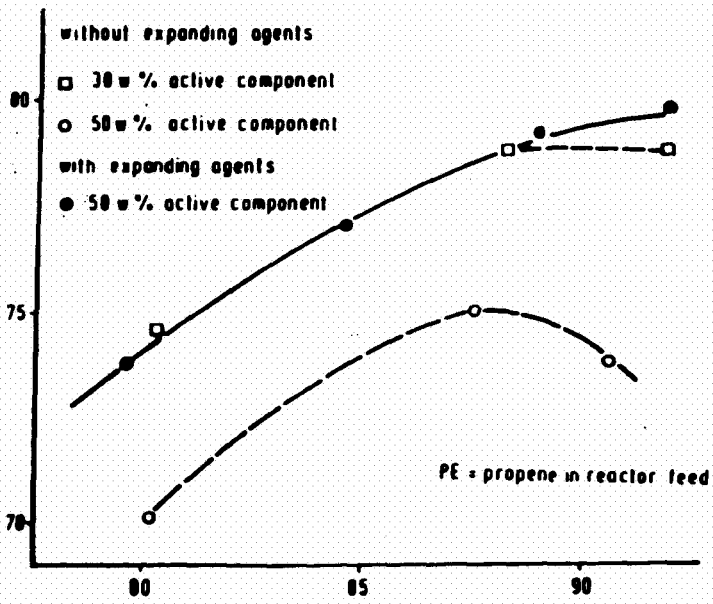

Add Figure 9 as shown below:

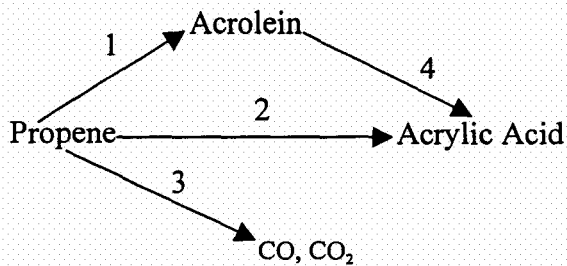

UNITED STATES PATENT AND TRADEMARK OFFICE
CERTIFICATE OF CORRECTION

PATENT NO. : 6,319,960 B1
APPLICATION NO. : 07/118619
DATED : November 20, 2001
INVENTOR(S) : William C. Behrmann et al.

It is certified that error appears in the above-identified patent and that said Letters Patent is hereby corrected as shown below:

In column 2, after line 67, insert:

--Figure 4 is a schematic representation of the process for preparing shell catalysts.

Figures 5A and 5B show temperature and moisture profiles during the coating process; time on the abscissa, air temperature in the drum, and wt% water in the exhaust gas on the ordinate of 5A and 5B, respectively.

Figure 6 shows optimum coating temperature profiles at different water contents of drying air coating time in minutes on the abscissa, exhaust temperature in °C on the ordinate.

Figure 7 shows the diameter distribution of shell catalysts prepared in different devices, diameter in mm on the abscissa, relative frequency in % on the ordinate.

Figure 8 shows pore diffusion limitation of shell catalysts for the propene oxidation to acrolein, where the abscissa is propene conversion [mol/100 mol PE] and the ordinate is acrolein yield [mol/100 mol PE].--

Figure 9 is a reaction scheme for the oxidation of propene.

In column 2, after line 56, insert:

SUMMARY

Shell catalysts were prepared by coating a catalytically active material onto a superficially rough inert support in a specific coating device. Even for thick shells with up to 70 % of the weight related to the final catalyst, high abrasion resistance was achieved. Catalyst properties are highly dependent on production parameters such as moisture control during coating, mechanical energy input through drum rotation, and adjustments for differing thermal expansion coefficients of the active material and the support. Selectively and kinetic studies of this catalyst show, that pore diffusion was suppressed by using expanding agents during the shell formation.

INTRODUCTION

The rate of diffusion limitation in heterogeneous oxidation reactions is widely discussed in literature. While some oxidation catalyst usually need only a low content of active catalyst phase, i.e., V-P-TiOx-catalysts for phthalic acid or maleic anhydrid, most bismuth-molybdate catalysts are bulk catalysts because of their lower activities. To avoid these diffusion limitation of those catalysts, in a large number of publications, various

UNITED STATES PATENT AND TRADEMARK OFFICE
CERTIFICATE OF CORRECTION

| | |
|---|---|
| PATENT NO. | : 6,319,960 B1 |
| APPLICATION NO. | : 07/118619 |
| DATED | : November 20, 2001 |
| INVENTOR(S) | : William C. Behrmann et al. |

It is certified that error appears in the above-identified patent and that said Letters Patent is hereby corrected as shown below:

proposals were made to get a better bismuth molybdate catalyst. Shell catalysts have promising properties: Pore diffusion rates are low because of the short diffusion paths for gaseous reactants. Local overheating is avoided by the temperature equalizing effects of the support material and the adaption of catalytic activity to the technically achievable heat transfer. The pressure drop in the reactor can be reduced by minimizing variations in pellet diameters. The quantity of expensive catalytically active material can be minimized to the requirements of the reaction kinetic.

In the production of thick shell catalysts - catalysts with a shell weight of more than 20% of the total catalyst -- the usual conventional coating processes result in a poor abration resistance of the shell, not satisfactory for use in fixed bed reactors, and in a too large variation in the pellet diameters.

To over come these insufficiencies, an improved process was developed.

EXPERIMENTAL

The new process was developed by using the advantages offered by devices designed for filmcoating of pellets, paticularly favorable is the Driacoater. A flow sheet of the process is given in Figure 4. The catalytic material in form of an oxidic prestage of the catalytically active phase, prepared by standard methods, is coated onto an inert support core.

In the first step, suspension of the powdered prestage is prepared by dispersing the powder in water. Sufficient water content of the suspension should allow a reliable continuous pumping and spraying operation. At the same time, it needs to be minimized for reducing the energy consumption for evaporation and to shorten the run time of the coating step. A typical water content is 40-50 weight percent relative to the catalyst. Usually 2-5 percent of binder, i.e., glucose, urea, etc., is added to the suspension to improve the abrasion resistance of the final catalyst. For the preparation of thick shell catalysts, an additional expanding material may be added to the suspension to increase the macroporosity of the final catalyst.

The coating procedure begins by loading the coater drum with the inert support. For oxidation reactions, the support should have a low surface area and an outer surface with a high degree of roughness to guarantee a firmly anchored shell to the support. Chemically, the support consist, i.e., of $\alpha$-$Al_2O_3$, Mg-silicates or Al-silicates. Next, the support is fluidized mechanically by rotating the drum and simultaneously loosened by drying air. The air is injected exclusively from the bottom of the fluidized bed through hollow ribs attached to the inside wall of the drum. The moisture-laden exhaust air is drawn off above the material through the hollow receiving lug of the rotation axis of the

UNITED STATES PATENT AND TRADEMARK OFFICE
CERTIFICATE OF CORRECTION

| | | |
|---|---|---|
| PATENT NO. | : 6,319,960 B1 | |
| APPLICATION NO. | : 07/118619 | |
| DATED | : November 20, 2001 | |
| INVENTOR(S) | : William C. Behrmann et al. | |

It is certified that error appears in the above-identified patent and that said Letters Patent is hereby corrected as shown below:

drum. The suspension is sprayed onto the fluidized bed by two component nozzles with a suspension pressure upstream of the nozzles of about 1 to 3 bar generated by a suspension pump. Therefore, the suspension is being sprayed in counter flow to the drying air, while the fluidized particle bed is moving across the flow of both streams. During the coating process, the flow rate and the temperature of the drying air is normally held constant at about 15-30 $Nm^3$/h per liter support and 80-100°C.

Smaller air throughputs result in distinctly slower drying rates, less uniform flow through the entire fluidized bend due to bypass at the drum wall and in substantially longer preparation times.

Higher air throughputs cause the suspension to dry out too rapidly on its way from the nozzle to the charge surface, causing a discharge of dried prestage powder with the exhaust air.

In order to achieve an abrasion resistant and rigidly anchored shell, the precise control of the shell humidity during coating is necessary. The moisture of the shell surface has to be held constant during the coating process. This can be readily controlled by the amount of suspension sprayed per unit of time. Both the air temperature above the charge and the humidity of the exhaust air, permit a sensitive control of the drying process. They can both be used as the measured variables to control the spraying process. These process parameters also allow a fully automatic spraying with the help of a suitable control algorithm that has been developed for this application.

This spraying operation is followed by a consolidation phase of 5 minutes while the drum continues to rate, and a drying phase of 20 minutes without continuous drum rotation. After air-drying over night, the catalyst is activated by conventional treatment at elevated temperature.

RESULTS AND DISCUSSION OF PREPARATION CONDITIONS

The coating process developed showed to be severely sensitive to variations in the process parameters:
- drying air: temperature, flow rate and moisture content
- suspension: flow rate, moisture content
- pan revolution and coating time
- properties of the support and of the prestage of the active catalyst powder.

UNITED STATES PATENT AND TRADEMARK OFFICE
CERTIFICATE OF CORRECTION

| | | |
|---|---|---|
| PATENT NO. | : 6,319,960 B1 | |
| APPLICATION NO. | : 07/118619 | |
| DATED | : November 20, 2001 | |
| INVENTOR(S) | : William C. Behrmann et al. | |

It is certified that error appears in the above-identified patent and that said Letters Patent is hereby corrected as shown below:

Moisture Control

While the drying air stream conditions are held constant, the process parameters during the coating process are controlled by the suspension flow rate. When the shell is too moist during coating, several particle agglomerate with one another causing the final diameter distribution to deteriorate. On the other hand, the desired anchoring of the shell to the support and the consolidation of the shell itself cannot be obtained if the shell gets too dry. Typical temperature profiles of the gas temperature above the fluidized bed during preparation are shown in Figure 5. Initially, the fresh air shows a sharp temperature drop. Later in the production cycle, there is a slight temperature decrease and the moisture content of the effluent exhaust increases at the same time.

While the suspension feed rate during the whole preparation periods stays constant, the moisture increase is caused by the removal of water from the inner shell. Therefore, the moisture content at the shell surface is different from the average moisture content of the shell.

This average moisture content was determined at different times during the coating process by taking samples, which were then dried until their weights stayed constant. A slight decrease in the shell moisture was observed, which is necessary to obtain highly abrasion resistant catalyst shells. The typical moisture content of the shell for the used multicomponent bismuthmolybdate catalyst powder shows about 30 weight percent of the shell material shortly after beginning of the coating process and decreases to about 20 weight percent of the production cycle.

Figure 5 also shows the narrow limits; the air temperature profiles above the fluidized bed need to be controlled in during the coating process. These profiles are examples of measurements taken inside the developmental machine, the Driacoater 500, with a load of 6 kg support and a drying air stream of 2 $Nm^3$/min and 80°C. They are directly transferable to production machines up to 300-500 kg capacity for one charge.

The pan temperature during the preparation of the two Samples No. 27 and No. 29 differs less than 1 degree when the moisture content of the fresh drying air was held at 1 vol. percent $H_2O$. Nevertheless, in Experiment No. 27, the shell moisture was found to be too high, caused by water not sufficiently being evaporated. The resulting abrasion resistance in Example No. 27 is very different from that in Example No. 29 with 7.0 vs. 2.0 weight percent*. On the other hand, in Trial No. 37, the shell was found to be too dry during coating and also the abrasion resistance is insufficient compared to Trial No. 35. This shows that the temperature profile needs to be adjusted, when the moisture content at the drying air varies.

UNITED STATES PATENT AND TRADEMARK OFFICE
CERTIFICATE OF CORRECTION

PATENT NO. : 6,319,960 B1
APPLICATION NO. : 07/118619
DATED : November 20, 2001
INVENTOR(S) : William C. Behrmann et al.

It is certified that error appears in the above-identified patent and that said Letters Patent is hereby corrected as shown below:

While the profile of No. 29 is optimal in respect to a moisture content of 1 percent of the drying air, it leads to a too dry shell for drying air having a moisture content of 2 vol. percent (Trial No. 37). As these examples show the exhaust air temperatures and moisture contents are very sensitive parameters in controlling the coating process. Both can be used in the automatization of the coating process: The amount of suspension sprayed is preferably adjusted to obtain the optimum temperature profile depending on the moisture content of the fresh drying air. Typical temperature profiles for 3 different drying air qualities are shown in Figure 6. At higher moisture contents, smaller suspension feed rates could be utilized resulting in an increased coating time. For the preparation of a catalyst with 50 percent active material, this time will increase from 50 minutes for 0.5 vol. % $H_2O$ in the drying air up to about 85 minutes for a 4 vol. % $H_2O$ content.

Mechanical Energy Input

If the preparation time exceeds specific values depending on powder properties and if the moisture content of the drying air is too high, the mechanical energy input may cause a too high of a consolidation of the shell. The shell forms very fine cracks, which enlarge with and increase of production time. This will cause a break of the shell during further processing of the catalyst and will lower its abrasion resistance.

---

*The abrasion resistance of the samples was tested after the final activation in the La Roche Friabilator (20 rotations per minute, running time of 7 minutes). It determines the loss in weight of the catalyst after the test relative to the weight of the fresh catalyst. For technical use, the abrasion resistance value should be less than 3 weight percent.

In Batch B, the coating duration was increased compared to Batch 1 by reducing the drying air stream.

This results in a lower abrasion resistance (Tab. 1). The same occurs, if the spraying process is followed by too long of a consolidation period with continued drum rotation (Batch B compared to Batch C).

UNITED STATES PATENT AND TRADEMARK OFFICE
CERTIFICATE OF CORRECTION

PATENT NO. : 6,319,960 B1
APPLICATION NO. : 07/118619
DATED : November 20, 2001
INVENTOR(S) : William C. Behrmann et al.

It is certified that error appears in the above-identified patent and that said Letters Patent is hereby corrected as shown below:

TABLE 1

Mechanical Energy Input During Preparation

| Batch No. | Coating Time (Min.) | Consolidation Time (Min.) | Abrasion Resistance (Weight %) |
|---|---|---|---|
| A | 65 | 5 | 1.3 |
| B | 105 | 5 | 7.6 |
| C | 65 | 15 | 4.5 |

Thermal Expansion Coefficient

During the process development, it was found that the thermal expansion coefficient of the powdered active material and the support material should be approximately equal. If these coefficients differ by a larger amount (more than 10-20 %), the shell will crack in the final temperings step of the catalyst activation. These cracks substantially reduce the abrasion resistance of the final catalyst: If the thermal expansion coefficients are very different from each other, the shell chips off in flakes. The increase in abrasion resistance with respect to the difference in expansion coefficients ffor three examples is given in Table 2.

TABLE 2
Influence of the Coefficient of Thermal Expansion on Abrasion Resistance of Final Catalyst

| Batch No. | Calcin. Temp. [°C] | Spec. Surface [m²/G] | Linear Expansion Coefficient (50 to 500°C) | | Abrasion Resistance [weight %] |
| | | | Catalyst Powder [$10^{-7}$/°C] | Support [$10^{-7}$/°C] | |
|---|---|---|---|---|---|
| D | 330 | 52 | n.m. | 71 | 35.2 |
| E | 450 | 35 | 41 | 71 | 8.7 |
| F | 520 | 23 | 77.3 | 71 | 0.6 |

The catalyst powder used for the sample preparations was a multicomponent bismuth molybdate with the composition $Mo_{12}$ Bi, Fe, $N1_{10}$ $CO_{o.3}$ $P_1$ Ox which was prepared by standard methods [8]. The support was the SA 5218 of Norton Comp. While suitable supports fall in the narrow range of about 70-90 x $10^{-7}$ / °C, it was found that the thermal expansion coefficients of prestage powder could be adjusted by temperature treatments at 250 to 600°C. For a catalyst powder calcinated at a temperature lower than 350°C (Batch D), the linear expansion coefficient changes widely during heating from 50&C up to 600° C. This coefficient could not be determined with standard equipment.

UNITED STATES PATENT AND TRADEMARK OFFICE
CERTIFICATE OF CORRECTION

PATENT NO. : 6,319,960 B1
APPLICATION NO. : 07/118619
DATED : November 20, 2001
INVENTOR(S) : William C. Behrmann et al.

It is certified that error appears in the above-identified patent and that said Letters Patent is hereby corrected as shown below:

The catalyst shells prepared from such a powder cracked during the activation. As the expansion coefficient difference is decreased by changing the calcination temperature, the abrasion resistance increases sharply (Table 2). Care must be taken that this treatment is being carried out not only for a specific temperature, but for the entire temperature range of the final activation operation.

Expanding Agents

A characteristic property of oxidation processes is pore diffusion limitation, which results in undesired combustion products such as carbon oxides. In the oxidation of propene to acrolein for example, it is observed that when with shell catalyst pore diffusion occurs, its influence increases with increasing shell thickness. The acrolein selectivity of a shell catalyst consisting of 50 percent active component, a usual value for catalyst in industrial application, is about 4 percent less than one with 38 percent (Figure 8). Pore diffusion may be sharply reduced by incorporating an expanding agent into the shell during production and by removing it later during the activation step. These agents can be easily incorporated if they are added to the suspension and thus are coated together with the catalytic powder. For this method, they should nearly be insoluble in the dispersing agent and be removable' from the formed shell by thermolysis or oxidation at temperatures below the activation temperature. Suitable materials are pentaerythritol, polymethacrylates, and polystyrene. Figure 8 shows a shell catalyst with 50 weight percent of active material prepared wit a 5 weight percent expanding pentaerythritol exhibits the same acrolein selectivities as a catalyst with 38 percent active material without expanding agent. This result is explained by a remarkable decrease of pore diffusion limitation by using expanding agents.

CATALYST PROPERTIES

Particle Size Distribution

The progress in the production of shell catalysts by using the new process is shown also by the narrow particle size distribution obtained. This size distribution sharply affects the pressure drop in a commercially used narrow tube reactor for oxidation reactions and so affects directly the energy costs of the processes.

Figure 4 shows the diameter distribution of samples made in a Driacoater and in a conventional rotating drum, where the drying air is not passing through the fluidized bed. Whereas the average diameter of the particles is bout 5.3 mm for both samples, the mean deviation of the conventional preparation is $s = 0.7$ mm; for the Driacoater preparation, it is $s = 0.3$.

UNITED STATES PATENT AND TRADEMARK OFFICE
CERTIFICATE OF CORRECTION

| | | |
|---|---|---|
| PATENT NO. | : 6,319,960 B1 | |
| APPLICATION NO. | : 07/118619 | |
| DATED | : November 20, 2001 | |
| INVENTOR(S) | : William C. Behrmann et al. | |

It is certified that error appears in the above-identified patent and that said Letters Patent is hereby corrected as shown below:

Kinetic Properties

Detailed studies of the evaluation of the reaction kinetics were carried out. The reaction scheme is depicted in Figure 9 and the obtained effective kinetic parameters are shown in Table 3 for catalysts with 30 and 50 weight percent active material, respectively. Both catalysts were prepared with pentaerythritol as an expanding agent, whereas all other preparation parameters were held constant.

TABLE 3

Results for Effective Kinetic Parameters $$r_{i,eff} = A_i \cdot \exp(-E_i/RT) \cdot P_{Pe}^{n_{i1}} \cdot P_{O_2}^{n_{i2}} \cdot P_{Ac}^{n_{i3}}$$

| i | active phase catalyst 30 weight % $A_i$ Kmole/$m^3$·s·Pascal$^{(\sum_j n_{ij})}$ | active phase catalyst 50 weight % $A_i$ Kmole/$m^3$·s·Pascal$^{(\sum_j n_{ij})}$ | $E_i$ J/Kmole | $n_{i1}$ | $n_{i2}$ | $n_{i3}$ |
|---|---|---|---|---|---|---|
| 1 | $16.7 \times 10^{-6}$ | $30.4 \times 10^{-6}$ | $47.4 \times 10^6$ | 0.44 | 0.93 | 0 |
| 2 | $1.3 \times 10^{-6}$ | $2.26 \times 10^{-6}$ | $42.8 \times 10^6$ | 0.54 | 0.54 | 0 |
| 3 | $1.28 \times 10^{-3}$ | $2.03 \times 10^{-3}$ | $52.8 \times 10^6$ | 0.66 | 0 | 0 |
| 4 | $77.1 \times 10^{-3}$ | $272.5 \times 10^{-3}$ | $93.2 \times 10^6$ | 0 | 0 | 1 |

It was surprising that for the three parallel reactions originating from propene, the activation energies Ei did not change, whereas the preexponential factors Ai increased by a conversion factor which was nearly equivalent to the increase of active material in the catalyst.

UNITED STATES PATENT AND TRADEMARK OFFICE
CERTIFICATE OF CORRECTION

PATENT NO.        : 6,319,960 B1
APPLICATION NO. : 07/118619
DATED             : November 20, 2001
INVENTOR(S)       : William C. Behrmann et al.

It is certified that error appears in the above-identified patent and that said Letters Patent is hereby corrected as shown below:

In claim 21, column 10, line 4, replace the word "cobalt" with --metal--.

In claim 22, column 10, line 8, replace the word "method" with --metal--.

Signed and Sealed this

Nineteenth Day of September, 2006

JON W. DUDAS
*Director of the United States Patent and Trademark Office*